US008282625B2

(12) United States Patent
Ullestad et al.

(10) Patent No.: US 8,282,625 B2
(45) Date of Patent: Oct. 9, 2012

(54) IMPLANTABLE MEDICAL DEVICE WITH TIME FOR THERAPEUTIC OUTPUT REPLENISHMENT DETERMINATION AND METHOD THEREFORE

(75) Inventors: David C. Ullestad, Maple Grove, MN (US); Mark J Bina, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 2894 days.

(21) Appl. No.: 10/836,589

(22) Filed: Apr. 30, 2004

(65) Prior Publication Data

US 2006/0149220 A1    Jul. 6, 2006

(51) Int. Cl.
*A61K 9/22* (2006.01)
*A61M 37/00* (2006.01)
*A61M 1/00* (2006.01)
(52) U.S. Cl. ............. 604/890.1; 604/131; 604/151
(58) Field of Classification Search ........ 604/890.1, 604/891.1, 131, 151; 700/90
See application file for complete search history.

(56) References Cited

U.S. PATENT DOCUMENTS

| 4,373,527 | A | 2/1983 | Fischell |
| 4,525,265 | A | 6/1985 | Abe et al. |
| 4,573,994 | A | 3/1986 | Fischell |
| 4,619,653 | A | 10/1986 | Fischell |
| 4,692,147 | A | 9/1987 | Duggan |
| 4,731,051 | A | 3/1988 | Fischell |
| 5,069,668 | A | 12/1991 | Boydman |
| 6,010,483 | A | 1/2000 | Spencer |
| 2001/0037083 | A1 * | 11/2001 | Hartlaub et al. ............ 604/65 |
| 2002/0087113 | A1 | 7/2002 | Hartlaub |
| 2002/0087115 | A1 | 7/2002 | Hartlaub |
| 2002/0087116 | A1 | 7/2002 | Hartlaub |
| 2003/0204274 | A1 | 10/2003 | Ullestad et al. |
| 2004/0122530 | A1 | 6/2004 | Hansen et al. |

FOREIGN PATENT DOCUMENTS

| DE | 3227518 A1 | 5/1983 |
| WO | WO 84/00493 | 2/1984 |
| WO | WO 84/03218 | 8/1984 |
| WO | WO01/34220 A2 | 5/2001 |
| WO | WO 02/072178 | 1/2002 |
| WO | WO 02/053213 | 7/2002 |
| WO | WO 2004/028596 | 4/2004 |

OTHER PUBLICATIONS

International Search Report, Application No. PCT/US2004/031664, mailed Feb. 23, 2005.

* cited by examiner

*Primary Examiner* — Nicholas Lucchesi
*Assistant Examiner* — Rebecca E Eisenberg
(74) *Attorney, Agent, or Firm* — IPLM Group, P.A.

(57) ABSTRACT

An implantable medical device for producing a variable therapeutic output to a patient. A therapeutic output delivery module requires replenishment following delivery of a predetermined amount of the therapeutic output. A calculator is responsive to a measure of an amount of the therapeutic output actually delivered to the patient for determining a parameter representative of a time at which the therapeutic output delivery module of the implantable medical device should be replenished with the therapeutic substance based at least in part upon the amount obtained from the measure. A method determines a parameter representative of a time at which a therapeutic output module of an implantable medical device should be replenished following delivery of a predetermined amount of therapeutic output. An amount of the therapeutic output actually delivered to the patient is measured. The parameter is calculated based at least in part upon the amount obtained in the measuring step.

54 Claims, 6 Drawing Sheets

IMPLANTABLE MEDICAL DEVICE WITH TIME FOR THERAPEUTIC OUTPUT REPLENISHMENT DETERMINATION AND METHOD THEREFORE

A portion of the disclosure of this patent document contains material that is subject to copyright protection. The copyright owner has no objection to the facsimile reproduction by anyone of the patent document or the patent disclosure, as it appears in the United States Patent and Trademark Office patent file or records, but otherwise reserves all copyright rights whatsoever.

FIELD OF THE INVENTION

The present invention relates to implantable medical devices and, more particularly to implantable medical devices which need to be replenished following delivery of a therapeutic output to a patient.

BACKGROUND OF THE INVENTION

Implantable medical devices for producing a therapeutic output to a patient are well known. Such devices include implantable devices that provide that provide an electrical stimuli to a patient, e.g., for soft tissue stimulation and/or pain control. Such devices also include implantable therapeutic substance delivery devices, e.g., devices capable of delivering a drug or other analgesia. Such implantable medical devices include implantable drug infusion pumps, implantable neurostimulators, implantable cardioverters, implantable cardiac pacemakers, implantable defibrillators and cochlear implants.

The therapeutic output, whether it is an electrical stimulus, a therapeutic substance or other therapeutic output, of a typical implantable medical device is exhaustible. That is, after having been implanted and providing a therapeutic output for a period of time, the medical device may need to be replenished in order to continue to deliver a therapeutic output. For example, a therapeutic substance delivery device may need a new supply of therapeutic substance or the therapeutic substance contained in the medical device for delivery may need to be replenished. If such a therapeutic substance is contained in a reservoir, the reservoir may need to be refilled. As another example, implantable medical devices generally need electrical power to operate. Such electrical power may be used to power electrical circuitry which operates the implantable medical device and/or may be used directly to provide electrical stimuli to a patient.

Since a typical implantable medical device has exhaustible resources, it may be important to ensure that the exhaustible resource is replenished before the resource has been exhausted in order to ensure continued, uninterrupted operation of the implantable medical device. To this end, some implantable medical devices have a mechanism that assists in determining when the exhaustible resource is close to being expended so that the resource may be replenished before exhaustion.

However, since the medical device is implanted subcutaneously in the patient, replenishment of the exhaustible resource may involve a surgical procedure to refill, recharge or even explant and re-implant the medical device. Thus, replenishment of an exhaustible resource in an implanted medical device may not be an act that is taken lightly.

The time at which an exhaustible resource in an implanted medical device is replenished can be extremely important. If the exhaustible resource is not replenished soon enough, the implanted medical device may stop functioning which could lead to deleterious and, possibly, disastrous, results. If, however, the exhaustible resource is replenished too soon, a surgical procedure may need to be performed before the surgical procedure is needed adding unnecessary risk, inconvenience and cost and, perhaps, requiring more surgery than otherwise would optimally be required.

It is typical to utilize a worst case scenario for determining when to replenish an exhaustible resource in an implanted medical device. Since it may be imperative not to allow an implanted medical device to completely exhaust an exhaustible resource, and possibly allow the implanted medical device to cease to perform its therapeutic function. The worst case scenario may depend upon variables in the construction and operation of the implanted medical device.

For example, if a chemical battery is an exhaustible resource of an implanted medical device, batteries employed in the construction of the medical device may have a tolerance in capacity. If so, it is typical to assume that the battery of any particular implantable medical device contains a battery having the minimum possible capacity within the tolerances allowed. Further, it may be typical to assume the most unfavorable tolerances of power consumption of the components of the implantable medical device. Still further, it may be typical to assume that the implanted medical device will generate the maximum possible stimuli. All of these assumptions taken together can ensure that the implanted medical device is replenished before it ceases to function. However, all of these assumptions taken together may also dictate a replenishment time which is substantially earlier than may be actually required.

As another example, if the implantable medical device is adapted to deliver a therapeutic substance to a patient, the amount of therapeutic substance actually delivered to the patient may depend upon many construction variables, including motor tolerances, and may also depend upon the number and amount of patient boluses delivered by the implanted medical device. It may be typical to assume the most unfavorable tolerances for medical device components and to assume the maximum number and volume of patient boluses in order to ensure that the implanted medical device is replenished before it ceases to function. Again however, all of these assumptions taken together may also dictate a replenishment time which is substantially earlier than may be actually required.

Accordingly, there is a need for an implantable medical device and method that addresses the above issues.

BRIEF SUMMARY OF THE INVENTION

The present invention solves these problems by providing an implantable medical device that can determine with greater accuracy than was previously possible the time at which the implantable medical device should be replenished. In an embodiment, the present invention provides an implantable medical that is responsive to the actual therapeutic output of the implantable medical device in order to more accurately determine the optimum replenishment time.

In an embodiment, the present invention provides an implantable medical device for producing a variable therapeutic output to a patient into which the implantable medical device is adapted to be implanted. A therapeutic output delivery module is adapted to be coupled to the patient and to deliver the variable therapeutic output to patient, the therapeutic output delivery module requiring replenishment following delivery of a predetermined amount of the therapeutic output. A measure is representative of an amount of the therapeutic output actually delivered to the patient. A calculator is responsive to the measure for determining a parameter representative of a time at which the therapeutic output delivery module of the implantable medical device should be replenished with the therapeutic substance based at least in part upon the amount obtained from the measure.

In another embodiment, the present invention provides an implantable drug pump for delivering a variable amount of a therapeutic substance to a patient into which the implantable drug pump is adapted to be implanted. A reservoir holds the therapeutic substance. A pump is operatively coupled to the reservoir and adapted to be coupled to the patient to deliver the therapeutic substance to the patient. A measure determines an amount based at least in part on an amount of the therapeutic substance actually delivered to the patient. A calculator is responsive to the measure for determining a time at which the reservoir of the implantable drug pump should be replenished with the therapeutic substance based at least in part upon the amount obtained from the measure.

In a preferred embodiment, the therapeutic output delivery module is a reservoir for holding a therapeutic substance and a pump operatively coupled to the reservoir for delivering the therapeutic substance to the patient.

In a preferred embodiment, the replenishment comprises replacing at least a portion of the therapeutic output delivery module.

In a preferred embodiment, the replenishment comprises replenishing a power source in the therapeutic output delivery module.

In another embodiment, the present invention provides an implantable medical device for producing a variable therapeutic output to a patient into which the implantable medical device is implanted. A therapeutic output delivery module is adapted to be coupled to the patient and to deliver the variable therapeutic output to patient, the therapeutic output delivery module requiring replenishment following delivery of a predetermined amount of the therapeutic output. A predetermined parameter is representative of a time at which the therapeutic output delivery module should be replenished based at least in part upon a predicted delivery rate of the therapeutic output to the patient. A measure determines an amount of the therapeutic output actually delivered to the patient. A comparator is operatively coupled to the predetermined parameter and to the measure for comparing the amount of the therapeutic output actually delivered to the patient with an amount of the therapeutic output expected to have been delivered to the patient based at least in part upon the predicted delivery rate and producing a result based thereon. An adjusted parameter is representative of an adjusted time at which the therapeutic output delivery module should be replenished based at least in part upon the result from the comparator.

In another embodiment, the present invention provides an implantable drug pump for delivering a variable amount of a therapeutic substance to a patient into which the implantable drug pump is implanted. A reservoir holds the therapeutic substance. A pump is operatively coupled to the reservoir and adapted to be coupled to the patient to deliver the therapeutic substance to the patient. A predetermined parameter is representative of a time at which the reservoir of the implantable drug pump should be replenished based at least in part upon a predicted delivery rate of the therapeutic substance to the patient. A measure determines an amount based at least in part on a quantity of the therapeutic substance actually delivered to the patient. A comparator is operatively coupled to the predetermined parameter and to the counter for comparing the amount with an amount of the therapeutic substance expected to have been delivered to the patient based at least in part upon the predicted delivery rate and producing a result based thereon. An adjusted parameter is representative of an adjusted time at which the reservoir of the implantable drug pump should be replenished with the therapeutic substance based at least in part upon the result from the comparator.

In a preferred embodiment, a communication module is operatively coupled to the parameter and capable of communicating the parameter to an external device.

In a preferred embodiment, the measure comprises a count of an amount of delivery of the pump.

In a preferred embodiment, the measure is a volume of the therapeutic substance.

In a preferred embodiment, the therapeutic output or therapeutic substance is delivered to the patient at a variable rate.

In a preferred embodiment, the variable rate is at least partially controlled by the patient.

In a preferred embodiment, the variable rate is at least partially determined by a patient-controlled bolus.

In a preferred embodiment, the determining is accomplished periodically.

In a preferred embodiment, the determining is accomplished daily.

In a preferred embodiment, the replenishment comprises refilling a reservoir with a therapeutic substance.

In a preferred embodiment, the calculator determines the parameter using simple arithmetic.

In a preferred embodiment, the simple arithmetic comprises addition and subtraction.

In a preferred embodiment, the adjusted parameter is determined by subtracting an amount from the adjusted parameter based at least in part on the result.

In a preferred embodiment, the subtracting decrements the adjusted parameter.

The present invention solves these problems by providing a method of determining a parameter associated with replenishment of an implantable medical device with greater accuracy than was previously possible. In an embodiment, the present invention provides a method of determining the parameter by being responsive to the actual therapeutic output of an implantable medical device in order to more accurately determine the optimum replenishment time.

In another embodiment, the present invention provides a method of determining a parameter representative of a time at which a therapeutic output module of an implantable medical device implanted in a patient should be replenished following delivery of a predetermined amount of therapeutic output. An amount of the therapeutic output actually delivered to the patient is measured. The parameter is calculated based at least in part upon the amount obtained in the measuring step.

In a preferred embodiment, the parameter is communicated to an external device.

In a preferred embodiment, the therapeutic output delivery module is a reservoir for holding a therapeutic substance and a pump is operatively coupled to the reservoir for delivering the therapeutic substance to the patient.

In another embodiment, the present invention provides a method of determining an adjusted parameter representative of a time at which a reservoir of an implantable drug pump implanted in a patient should be replenished with a therapeutic substance. An initial parameter representative of an initially estimated time at which the reservoir of the implantable drug pump should be replenished with the therapeutic substance based at least in part upon a predicted delivery rate of the therapeutic substance to the patient is determined. An amount is measured based at least in part on a quantity of the therapeutic substance actually delivered to the patient. The amount is compared with an amount of the therapeutic substance expected to have been delivered to the patient based upon the predicted delivery rate. The adjusted parameter is determined based at least in part upon a result of the comparing step. The adjusted parameters is communicated to an external device.

In a preferred embodiment, the measuring step comprises measuring an amount of delivery of the pump.

In a preferred embodiment, the measuring step comprises measuring a volume of the therapeutic substance.

In a preferred embodiment, wherein the therapeutic output is delivered to the patient at a variable rate.

In a preferred embodiment, the variable rate is at least partially controlled by the patient.

In a preferred embodiment, the variable rate is at least partially determined by a patient-controlled bolus.

In a preferred embodiment, the calculating step uses simple arithmetic.

In a preferred embodiment, the simple arithmetic comprises addition and subtraction.

In a preferred embodiment, the adjusted parameter is determined by subtracting an amount from the adjusted parameter based at least in part on the result.

In a preferred embodiment, the subtracting decrements the adjusted parameter.

DETAILED DESCRIPTION OF THE INVENTION

The present invention has applicability of multiple types of implantable medical devices including implantable medical devices providing electrical stimuli, e.g., an electrical stimulus to soft tissue and implantable medical devices that deliver a therapeutic substance, e.g., a drug delivery device.

Although the present invention is described primarily in terms of an implantable therapeutic substance delivery device and associated method, it is to be recognized and understood that the present invention may be equally described in terms of an implantable medical device delivering electrical stimuli to a patient and associated method. Both devices provide a therapeutic output to a patient through a delivery module. A therapeutic substance delivery device is described primarily in terms of the reservoir of therapeutic substance as an exhaustible resource. It is to be recognized and understood that the present invention may be equally described in terms of power, or another resource, of an electrical tissue stimulator as an exhaustible resource. The common thread, of course, is an exhaustible resource related to an implanted medical device and the need to rather accurately predict the time of replenishment of the exhaustible resource in order, in part, to ensure the continued operability of the implanted medical device and conservation of patient inconvenience, expenditure of medical resources and elimination of unneeded surgery.

A typical therapeutic substance delivery device has a therapeutic output delivery module adapted to provide a therapeutic output to a patient. An exemplary therapeutic output delivery module could operate by delivering a therapeutic substance to the patient. The therapeutic output delivery module could have a reservoir for holding therapeutic substance such as a drug, e.g., an analgesic, a pump for controlling the dispensing of the therapeutic substance, preferably at a controlled and possibly variable rate, and a catheter for delivering the dispensed therapeutic substance to a location in the body of the patient. A control module in the therapeutic substance delivery device is operably coupled to the therapeutic output delivery module and specifies the amount and the rate of delivery of the therapeutic substance. Typically, the control module is capable of being programmed, usually by a medical professional. The control module may allow the possibility of patient boluses. For example, the patient may optionally administer an additional dose or doses, or an increased dose or doses, e.g., for pain control. A patient who can administer optional doses of pain medication may actually use less medication than patient's who do not have such control.

Figure 1:
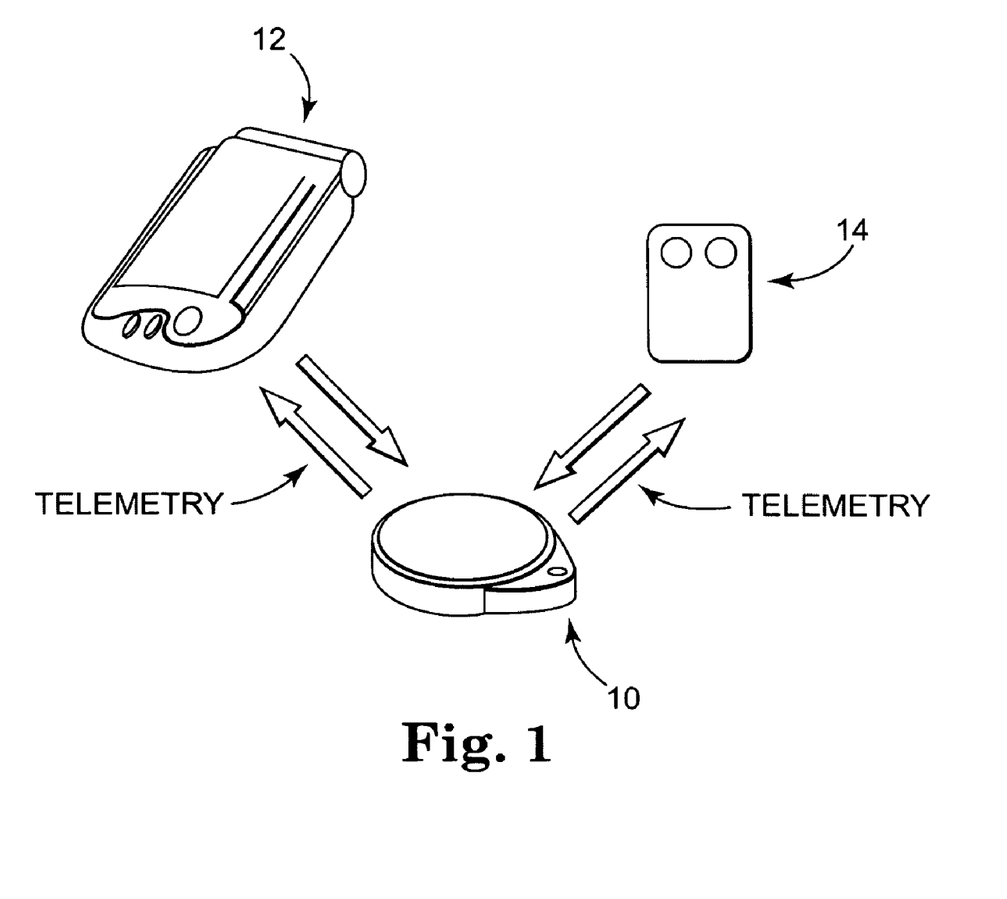
FIG. 1 is an exemplary embodiment of the external programming device and the external patient control communicating with the pump mechanism via telemetry.

An exemplary programmable drug delivery system allowing patient boluses is illustrated in FIG. 1. An implantable, programmable pump mechanism 10 has a control system that controls the operation of the pump mechanism. The control system includes a microprocessor and a memory programmable with selected functions for controlling the operation of the pump mechanism. The memory stores the programs and data related to the operation of the pump mechanism. The memory is coupled to the microprocessor, which in turn runs the desired operating programs that control the operation of the pump mechanism.

Access to the microprocessor is provided through a communications port located in the pump mechanism. The communication port receives and transmits information from/to an external programming device 12 or an external patient control device 14 via telemetry. FIG. 1 depicts the pump mechanism 10 and the external programming device 12 and patient control device 14 communicating via telemetry. This feature allows for the downloading and uploading of any or all information from the memory of the microprocessor to the programming devices.

Figure 2:
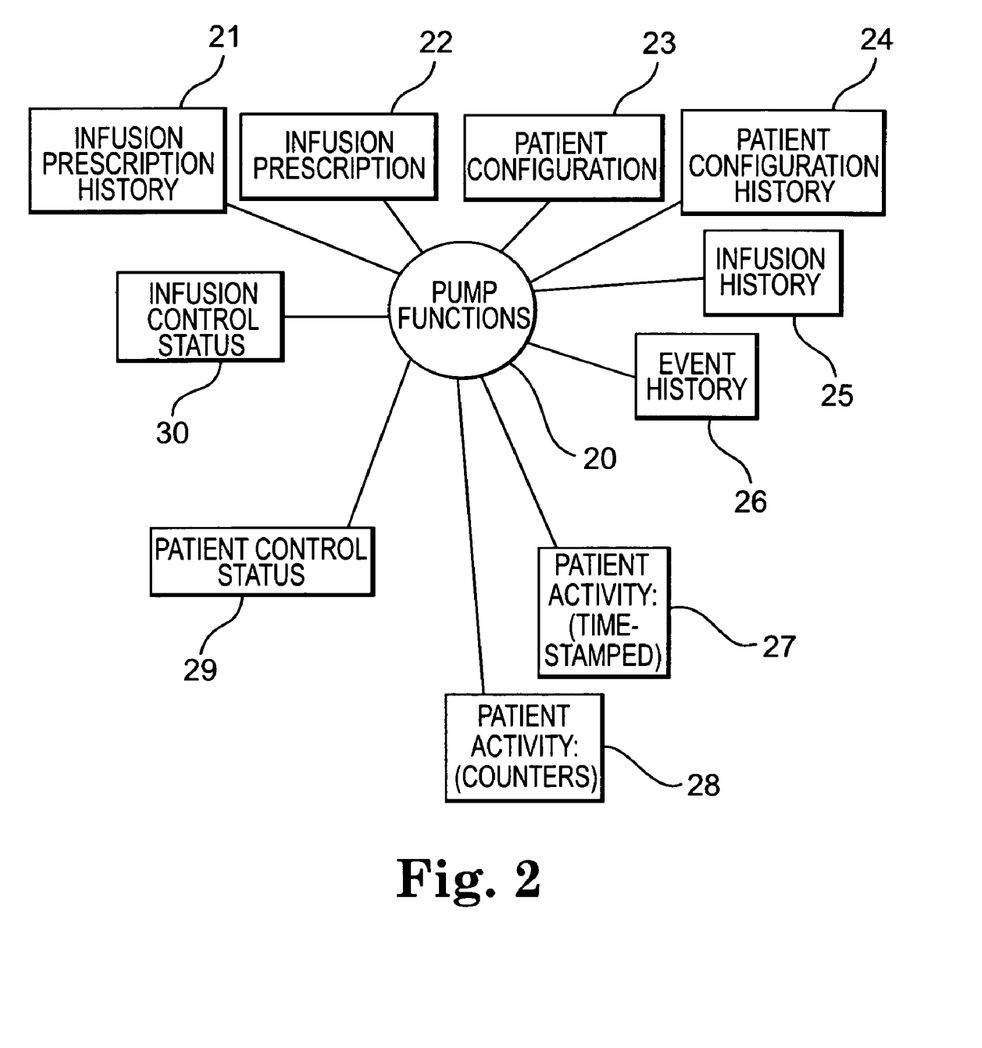
FIG. 2 depicts exemplary functions of the pump mechanism.

In FIG. 2, exemplary functions of the control system of the pump mechanism 10 are generally depicted. The function of the control system 20 generally include infusion prescription history 21, infusion prescription 22, patient configuration 23, patient configuration history 24, infusion history 25, event history 26, time-stamped patient activity 27, patient activity counter 28, patient control status 29, and infusion control status 30. The infusion prescription history 21, infusion prescription 22, patient configuration 23, and patient configuration history 24 are entered via the programmer 12 and downlinked into the pump mechanism. The infusion history 25, event history 26, patient activity time-stamped 27, and patient activity counter 28 are functions of the pump mechanism that are managed by the pump and are accessible via the programmer 12. These functions are able to be cleared by the programmer 12. The patient control status 29 and infusion control status 30 are also functions of the pump mechanism that are managed by the pump and are accessible via the programmer 12. However, these functions are not alterable by the programmer 12.

Initially, the system of the present invention is presented to a physician in an initial default state where all pump functions are disabled. Using the external programming device 12, the physician programs the initial patient infusion prescription. The prescription may be a fixed rate prescription that does not vary over time, unless changed by the physician or patient. Alternatively, the prescription may be multi-step where the infusion rate automatically adjusts over time. The infusion prescription history (a record of a given number of past prescriptions) is stored in the memory of the pump mechanism and may be managed and retrieved via the external programming device 12.

The physician also programs the pump mechanism to have a specific patient configuration by selecting which pump functions are enabled and selecting the parameters for each enabled pump function. If the physician enables a pump function, the physician must specify all of the programmable parameters associated with that pump function since the pump assumes no default values. The patient configuration containing the pump functions and related parameters is stored in the memory of the pump mechanism and can only be changed by the physician. The patient configuration can be read, cleared, or adjusted by the physician using the external programming device 12.

When the patient configuration is programmed into the pump mechanism, the patient configuration is time stamped according to the pump mechanism's current time/date setting contained in the pump mechanism's memory. As a result, the physician may easily identify when the patient configuration was entered or programmed into the pump mechanism. Should the physician need to enter a new patient configuration into the pump mechanism, the previous or old patient configuration is copied and recorded in a patient configuration history stored in the pump mechanism's memory. Each time the physician downlinks or programs a new patient configuration into the pump mechanism, the old or previous patient configuration, including all time/date stamped information, is automatically stored in the patient configuration history.

Depending on the patient configuration prescribed by the physician, certain pump functions may be available to the patient via the external patient control device 14. Like the external programming device 12, the external patient control device 14 is a hand held controller that communicates with the pump mechanism via telemetry. The pump functions that the physician may make available to the patient via the patient control device 14 may include: stop pump; re-start pump; increase current pump rate; decrease current pump rate; patient bolus, stop/cancel patient bolus, status summary; test pump alarm; silence pump alarm; and set event. These pump functions are explained in greater detail below. Some or all of these functions are available to the patient and may be used by the patient to vary their therapy based on their current/planned activity or personal assessment of "how they are feeling."

Figure 3:
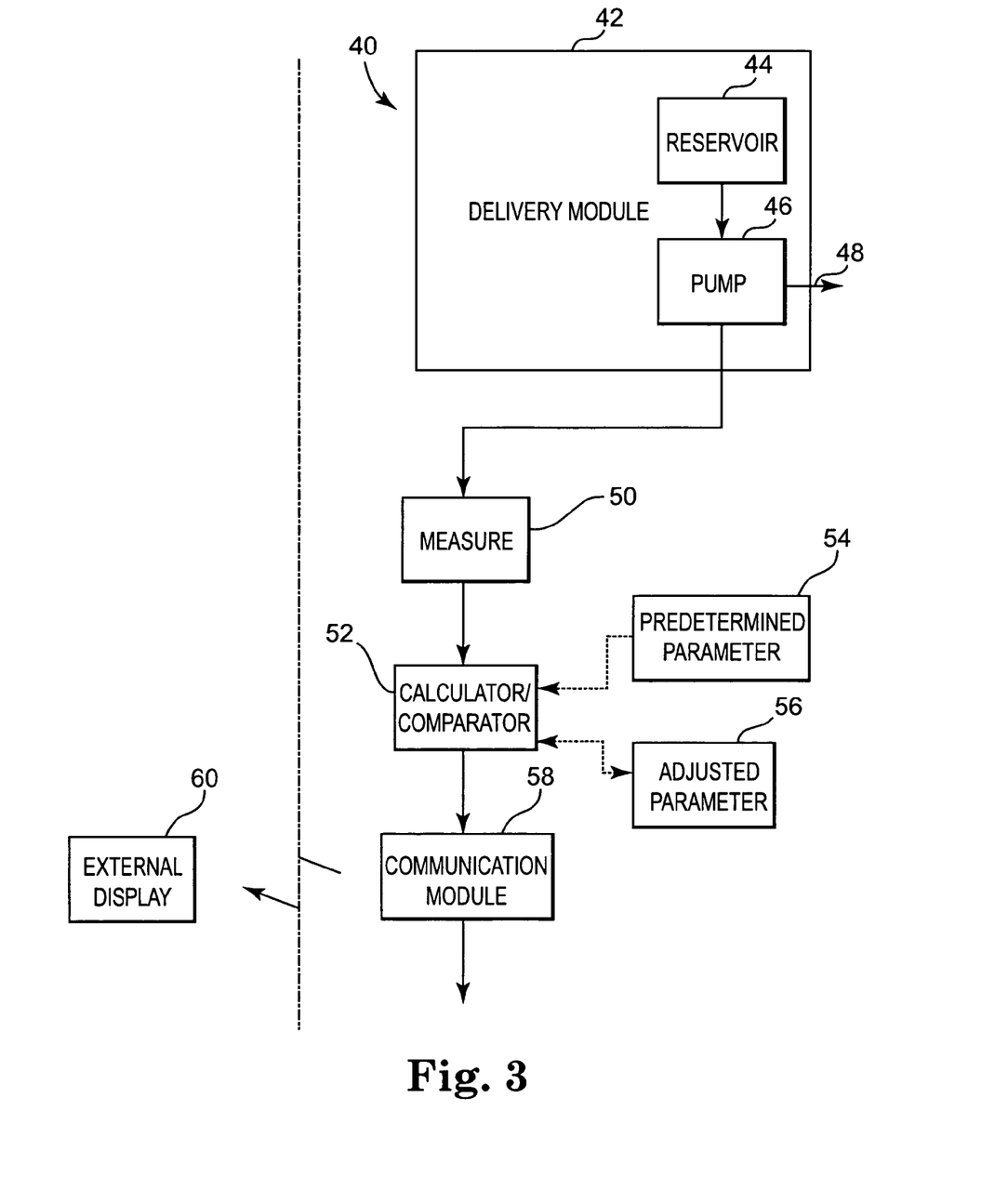
FIG. 3 is a partial functional block diagram of implantable medical device and communication components in accordance with an embodiment of the present invention.

FIG. 3 is a partial block diagram of implantable medical device 40 which is similar to programmable pump mechanism 10 described above. Basic device components such as those described with respect to FIG. 1 are also contained in implantable medical device 40. Similarly, most basic functions such as those described with respect to FIG. 2 are also contained in implantable medical 40 or associated components such as external programmers and controllers. FIG. 3, however, describes in more detail components of implantable medical device 40 that are significantly different in embodiments of the present and that obtain the considerable advantages of the present invention. Everything to the right of the vertical line in FIG. 3 is preferably contained subcutaneously and everything to the left of the vertical line is expected to be external.

Therapeutic output delivery module 42 is a portion of implantable device 40. It is to be recognized and understood that implantable medical device also includes other components which are typically required for operation in an implantable medical device 40 including a power source, control circuitry and communication circuitry. These components are conventional in nature and are not specifically illustrated here for clarity of illustration.

Therapeutic output delivery module 42 in this specific preferred embodiment is a drug infusion delivery module containing reservoir 44 for storing a supply of therapeutic substance for subsequent delivery to a patient and pump 46 for pumping the supply of therapeutic substance from reservoir 44 through catheter 48 to a delivery site in a patient. Pump 46, of course, is under control of electronics (not shown). Reservoir 44, pump 46, catheter 48 and the remainder of therapeutic output delivery module are conventional in nature and are well known in the art.

Measure 50 is operatively coupled to therapeutic output delivery module 42 and is responsible for measuring, in a reasonably accurate manner, the amount of therapeutic output, e.g., therapeutic substance, actually delivered to a patient. The amount of therapeutic output actually delivered, of course, can vary significantly from a predicted, an expected or a worst case of an amount of therapeutic output. As noted above, the predicted, expected or worst case amount can be determined by a wide variety of factors and, given the importance of not running short of therapeutic output, is generally conservatively determined. For example, it may be assumed that a patient exercises every possible bolus that the patient can control at every earliest opportunity for so doing. Such a determined of an amount of therapeutic output expended is, of course, conservative and is designed to ensure that implantable medical device 40 does not exhaust therapeutic output. However, the actual number of boluses elected by the patient is often quite fewer than the maximum allowed. If this is the case, then the amount of therapeutic output actual expended may be much less than the maximum amount allowed.

The exact mechanism for measuring the amount of therapeutic output is determined, at least in part, by the type of therapeutic output being supplied by therapeutic output delivery module 42. In the preferred embodiment of a therapeutic substance delivery module using pump 46, a preferred method is to count the number pump impulses or pumping steps incurred by pump 46. Since it is known how much therapeutic substance is delivered for each step of pump 46, in fact this is typically a method used to control the amount of delivery of output module 42, knowing the number of steps results in knowing the amount of therapeutic substance delivered. Alternatively, it may be possible to measure the amount of energy consumed by pump 46 since each pump step consumes are relatively constant amount of energy. Also alternatively, any type of flow or volume meter acting directly on the flow of therapeutic substance from output module 42 could also be utilized. If therapeutic output delivery module 42 provides an electrical output signal, it is possible to measure the amount of energy expended by output module 42, similar to measuring the amount of energy consumed by pump 46 in the example above but more direct. Coulomb counters are well known and are commonly employed for this purpose. Certainly other measures of measurement are known and expected without departing from the scope of the invention.

Calculator and/or comparator 52 receives the amount of therapeutic output actually delivered to the patient, or a relatively close approximation thereto, and, in one embodiment, calculates a time at which the therapeutic output should be replenished. By time in this instance it is meant a time in the future, i.e., a point in the future. This point could be identified by a specific date, for example, by a month and year, by a year or, perhaps, even a day and time of day. The granularity of the time of replenishment can vary by many factors including the overall lifespan of the therapeutic output before exhaustion. That is, if therapeutic output is expect to last for years, then a calculation of replenishment time could reasonably be determined by a month and year, or by a specific date or range of dates, if desired. The time of replenishment also depends on the safety margin to be employed which will vary by type of therapeutic output, the purpose of the therapeutic output, rate of use, lead time in scheduling replenishment and physician/clinician comfort in the safety margin. It is preferred that some reasonable safety reserve of therapeutic output be retained for safety of the patient. Although it could be, it is not usually contemplated that the time of replenishment would coincide with the time of exhaustion.

Many forms of relatively straight forward calculation methods are contemplated. For example, since the beginning amount of therapeutic output can be known (when loaded, for example), knowing an amount of therapeutic output actually used allows calculator 52 to determine an amount of therapeutic output remaining by subtraction. Calculator 52 may then calculate a time to replenishment by dividing the amount of therapeutic output remaining (adjusting for a reserve, if desired) by the rate at which the therapeutic output is being used. The rate used in the calculation can be a real time actual usage rate based on current consumption, an average or moving average based on consumption over a predetermined period of time, e.g., last thirty days, or a maximum rate at which therapeutic output can be consumed, as examples. The latter, maximum rate, of course, would again result in a worst case scenario but will have adjusted for the actual amount previously consumed. This may result in a much more accurate calculation of replenishment time than having assumed a worst case scenario over the entire lifetime of therapeutic output supply. It is to be recognized and understood, however, that other well known techniques for calculating remaining life of a consumable object based on knowing the actual amount of consumable remaining, or a close approximation thereto, can be used and are within the scope of the present invention.

Such calculation can occur in continuously in real time as new data is available, for example both amount of therapeutic output remaining and usage rate, or could occur periodically, either on a pure periodic basis such a daily or after a certain amount or a certain percentage of therapeutic output is consumed. These are just examples, of course, and other calculation iterations are also contemplated.

In an alternative embodiment, calculator/comparator 52 is supplied with a predetermined parameter 54 representative of an expected time of replenishment. Such parameter may be established, for example, when a supply of therapeutic output is loaded or added to implantable medical device 40. As an example, if reservoir 44 is filled with 100 milliliters of therapeutic substance and the worst case known usage rate, assuming all variables such as number and volume of boluses, pump variations, power variations, etc., is 0.1 milliliters per day, it can be assumed that in the worst case a 1,000 day supply of therapeutic substance is available. If it is desired that maintain an ten percent (10%) reserve (as an example only), then 900 days of therapeutic output would be available before replenishment. This parameter or a parameter determined in any other fashion can be used as a predetermined parameter. It is expected that predetermined parameter will, in fact, have some relationship to the expected lifetime supply of therapeutic output.

Predetermined parameter 54 may be characterized in many formats. As discussed above, predetermined parameter may be represented as a period of time, e.g., days, until replenishment. This information may be useful to a patient in determining when to schedule an appointment for replenishment. It is preferred, however, that predetermined parameter to converted to a calendar day (or week or month) for replenishment. This conversion can be accomplished in implantable medical device 40 or, preferably, can simply be supplied to implantable medical device 40, preferably at or around the time of loading or adding therapeutic output. It is to be recognized and understood that other forms and formats of predetermined parameter are also contemplated. For example, predetermined parameter 54 could be determined at the factory upon or shortly after manufacture. If the maximum capacity of reservoir 44 is known and the maximum pumping rate of pump 46 is known, then a worst case scenario for implantable medical device can be pre-established at or near the time of manufacture.

It is also contemplated that calculator 52 could first calculate a time for replenishment and that time could then subsequently be used as predetermined parameter 54.

If predetermined parameter 54 is available to calculator/comparator 52, calculator/comparator 52 may operate as a comparator. Instead of calculating a new time for replenishment, calculator/comparator 52 may more simply just adjust existing parameter 54 based upon the usage rate of therapeutic output delivery module 42. Using the example from above, the time for replenishment, i.e., predetermined parameter 54, has been set at 900 days. If it is known that this parameter was initially calculated based upon a maximum usage rate of 0.1 milliliters per day, then an actual usage rate of less than 0.1 milliliters per day can result in an adjustment being made to predetermined parameter 54. For example, every time 0.01 milliliters of therapeutic substance is saved from being delivered, one (1) day of extra time to replenishment is gained. In a preferred embodiment, the amount of therapeutic output per unit time, e.g., every day, is determined and every time a day's worth of therapeutic output is saved beyond the assumption, then one (1) day is added to the predetermined parameter 54. If predetermined parameter 54 is kept in a number of days to replenishment format, then one is simply added. If predetermined parameter 54 is kept in a date format, for example, the date is incremented by one day. Other formats and increments are contemplated.

The significant advantage of calculating by incrementation is that a much simpler calculator 52 is required. Since implantable medical device 40 has very little space and very little resources, it is much more practical to equip calculator 52 with an adder/subtractor than with a multiplier/divider.

The incremented or adjusted parameter 56 can be stored separately as illustrated in FIG. 3 or, alternatively, the adjusted parameter 56 can simply write over or otherwise replace predetermined parameter 54. In this case, adjusted parameter 56 would simply take the place of predetermined parameter 54 for all subsequent calculations (additions).

Communications module 58 is used to communicate, for example by telemetry, with an external device 60 used to inform the patient or medical professional or care giver of the time for replenishment. External device 60 could be any sort of conventional display, for example, or other communication tool. It is also contemplated that communication could be transcutaneous as, for example, by audible signals generated directly by communications module 58 and heard externally. Communication is conventional in nature and is well known in the art.

Figure 4:
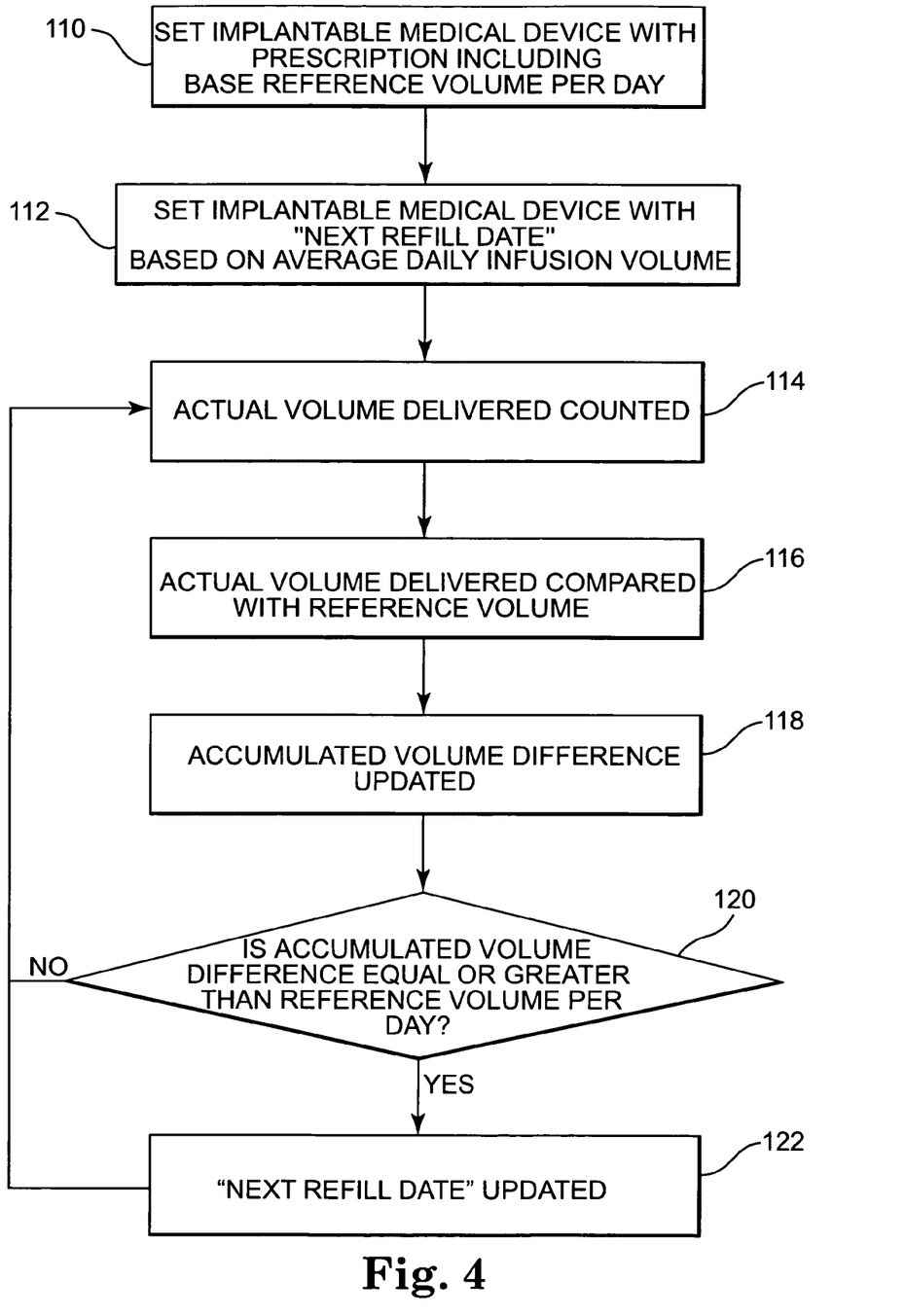
FIG. 4 is a flow chart illustrating a preferred embodiment of the present invention.

FIG. 4 is a flow chart illustrating an embodiment of the present invention. Implantable medical device 40 is programmed (110) with a delivery prescription including a base reference volume per day. Implantable medical device (112) is also programmed with a "Next Refill Date" based upon average daily infusion volume. The actual volume delivered is counted (114), e.g., by counting steps of pump 46, to determine the actual volume delivered. The actual volume delivered is compared (116) with a reference volume based on the average daily rate. The difference is accumulated (118) is updated on a periodic basis, e.g., continuously or daily. A comparison is made (120) to see if the accumulated difference is equal or greater to the reference volume per day. If not, the actual volume continues to be counted (114). If it is, the "Next Refill Date" is updated, e.g., incremented (122). The process then returns to counting (114) the actual volume.

Figure 5:
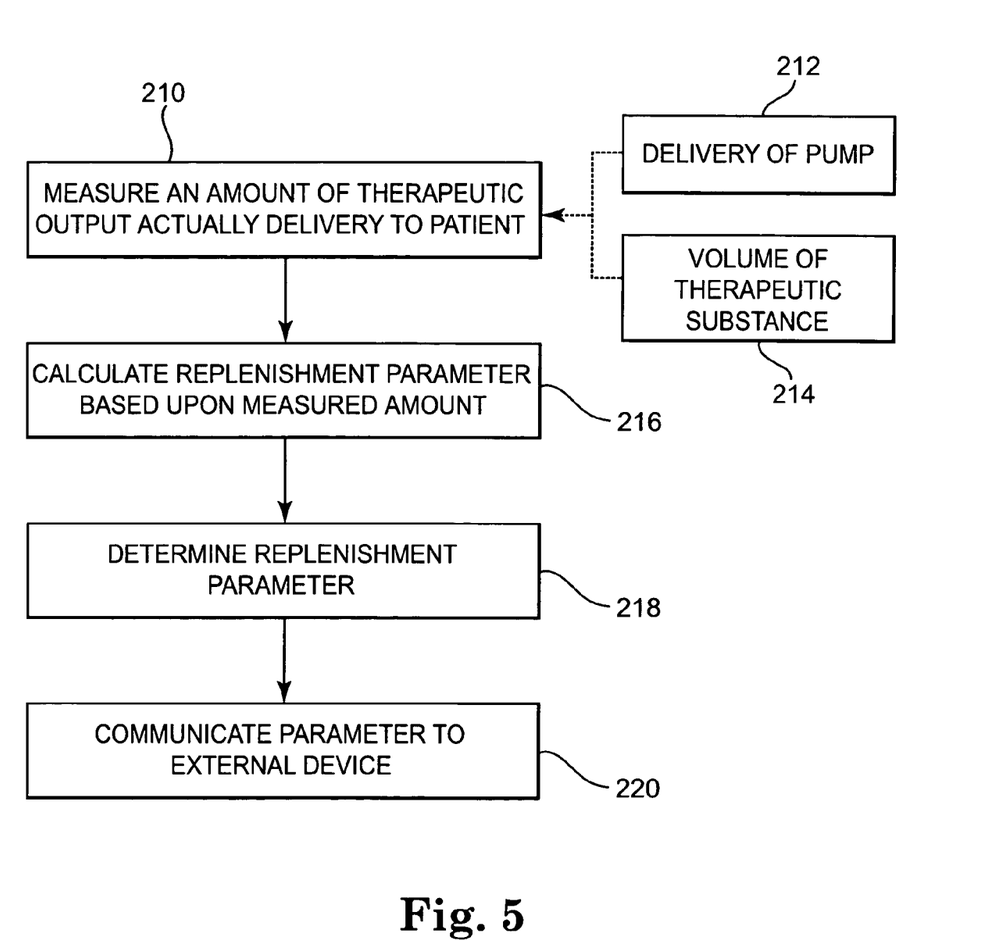
FIG. 5 is a flow chart illustrating an alternative embodiment of the present invention.

FIG. 5 is a flow chart illustrating an embodiment of the present invention in a different format. The amount of therapeutic output actually delivered to a patient is measured (210). This measurement (210) can be obtained either from measuring (212) the operation of pump 46 or from measuring (214) the volume of therapeutic substance, as examples. A replenishment parameter is calculated (216) based upon the measured (210) amount. A parameter representative of a time of replenishment is determined (218). The parameter is communicated (220) to an external device or an external person.

Figure 6:
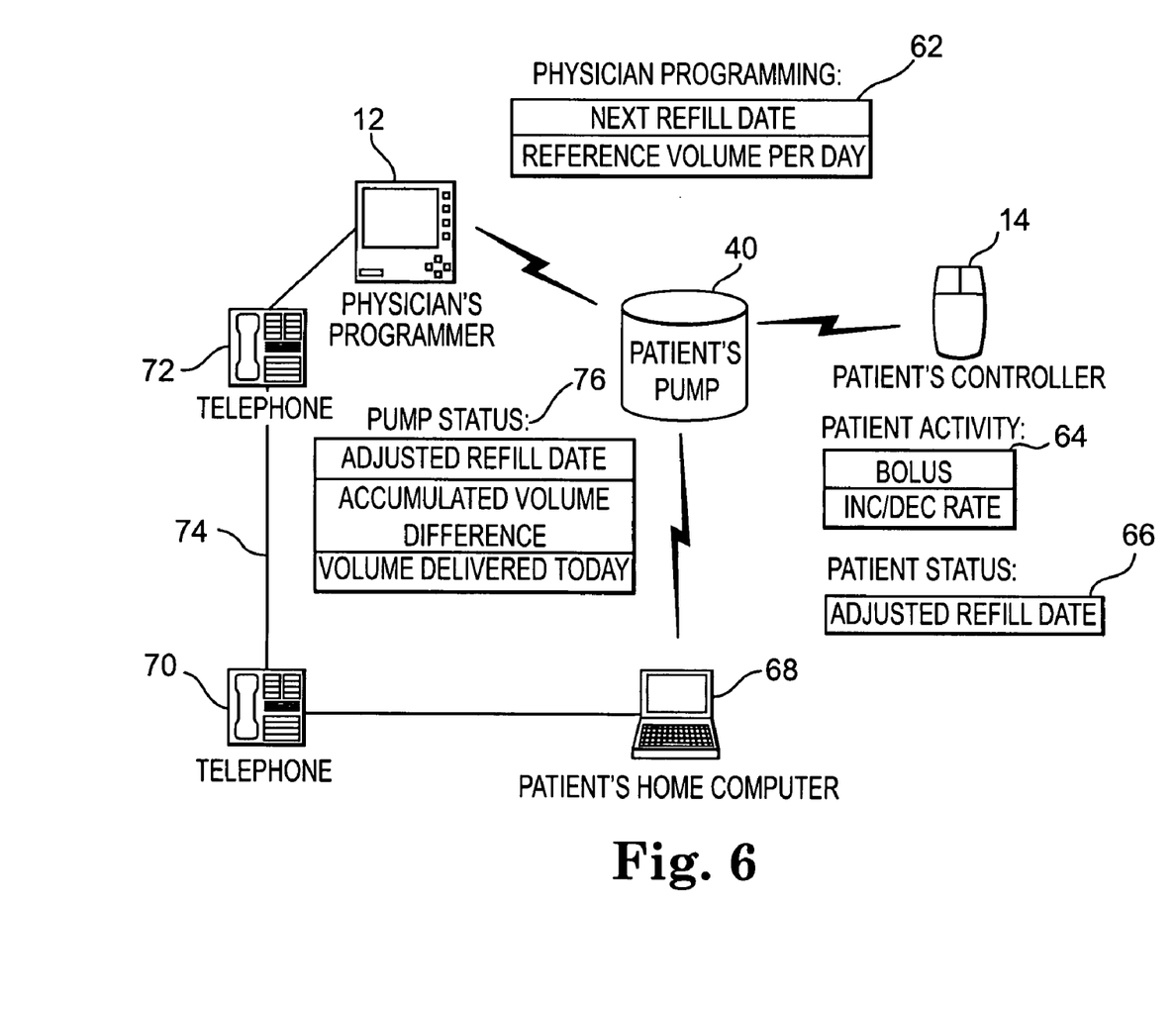
FIG. 6 is a function schematic illustrating communication related to the present invention.

FIG. 6 illustrates functional components beyond implantable medical device 40 and illustrates the cooperation and communication between various components and various individuals involved in the care of the patient. External programming device 12 can be used by a medical professional, e.g., a physician or clinician, to initially program implantable medical device 40 establishing a "Next Refill Date" and a "Reference Volume Per Day" (collectively 62). The patient interacts with implantable medical device 40, e.g., by self-administering boluses, with external patient control device 14 using patient activity controls 64. Patient also has available a patient status display 66 indicating the adjusted refill date.

Implantable medical device 40 can communicate with home computer 68 by any of a variety of well established communication techniques such as the Blue Tooth communication protocol. Home computer 68 can update the physician's external programming device 12 through of a number of established communication protocols including internet and dial-up telephone access using telephones 70 and 72 and telephone network 74. Among the information that can be transmitted to the physician via external programming device 12 (or other device capable of communicating with the physician) is pump status information 76 including the adjusted refill date (so the physician can contact the patient and schedule a refill appointment), the accumulated difference volume and the volume delivered in a unit of time, e.g., volume delivered daily.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device for producing a variable therapeutic output to a patient into which said implantable medical device is adapted to be implanted, comprising:

a therapeutic output delivery module adapted to be coupled to said patient and to deliver said variable therapeutic output to patient, said therapeutic output delivery module requiring replenishment following delivery of a predetermined amount of said therapeutic output;

a measure of an amount of said therapeutic output actually delivered to said patient; and a calculator responsive to said measure for determining a parameter representative of a time in the future at which said therapeutic output delivery module of said implantable medical device should be replenished with said therapeutic substance based at least in part upon said amount obtained from said measure.

2. An implantable medical device as in claim 1 further comprising a communication module operatively coupled to said parameter and capable of communicating said parameter to an external device.

3. An implantable medical device as in claim 1 wherein said therapeutic output delivery module comprises a reservoir for holding a therapeutic substance and a pump operatively coupled to said reservoir for delivering said therapeutic substance to said patient.

4. An implantable medical device as in claim 3 wherein said measure comprises a count of an amount of delivery of said pump.

5. An implantable medical device as in claim 3 wherein said measure comprises a volume of said therapeutic substance.

6. An implantable medical device as in claim 1 wherein said therapeutic output is delivered to said patient at a variable rate.

7. An implantable medical device as in claim 6 wherein said variable rate is at least partially controlled by said patient.

8. An implantable medical device as in claim 7 wherein said variable rate is at least partially deteimined by a patient-controlled bolus.

9. An implantable medical device as in claim 1 wherein said determining is accomplished periodically.

10. An implantable medical device as in claim 9 wherein said determining is accomplished daily.

11. An implantable medical device as in claim 1 wherein said replenishment comprises refilling a reservoir with a therapeutic substance.

12. An implantable medical device as in claim 1 wherein said replenishment comprises replacing at least a portion of said therapeutic output delivery module.

13. An implantable medical device as in claim 1 wherein said replenishment comprises replenishing a power source in said therapeutic output delivery module.

14. An implantable drug pump for delivering a variable amount of a therapeutic substance to a patient into which said implantable drug pump is adapted to be implanted, comprising:

a reservoir for holding said therapeutic substance;

a pump operatively coupled to said reservoir and adapted to be coupled to said patient to deliver said therapeutic substance to said patient;

a measure determining an amount based at least in part on an amount of said therapeutic substance actually delivered to said patient; and a calculator responsive to said measure for determining a time in the future at which said reservoir of said implantable drug pump should be replenished with said therapeutic substance based at least in part upon said amount obtained from said measure.

15. An implantable drug pump as in claim 14 further comprising a communication module operatively coupled to said time and capable of communicating said time to an external device.

16. An implantable drug pump as in claim 14 wherein said measure comprises a count of an amount of delivery of said pump.

17. An implantable drug pump as in claim 14 wherein said measure comprises a volume of said therapeutic substance.

18. An implantable drug pump as in claim 14 wherein said therapeutic substance is delivered to said patient at a variable rate.

19. An implantable medical device as in claim 18 wherein said variable rate is at least partially controlled by said patient.

20. An implantable medical device as in claim 19 wherein said variable rate is at least partially determined by a patient-controlled bolus.

21. An implantable drug pump as in claim 14 wherein said determining is accomplished periodically.

22. An implantable drug pump as in claim wherein 21 said determining is accomplished daily.

23. An implantable drug pump as in claim 14 wherein said replenishment comprises refilling said reservoir with a therapeutic substance.

24. An implantable medical device for producing a variable therapeutic output to a patient into which said implantable medical device is implanted, comprising:
   a therapeutic output delivery module adapted to be coupled to said patient and to deliver said variable therapeutic output to patient, said therapeutic output delivery module requiring replenishment following delivery of a predetermined amount of said therapeutic output;
   a predeteimined parameter representative of a time in the future at which said therapeutic output delivery module should be replenished based at least in part upon a predicted delivery rate of said therapeutic output to said patient;
   a measure determining an amount of said therapeutic output actually delivered to said patient;
   a comparator operatively coupled to said predetermined parameter and to said measure for comparing said amount of said therapeutic output actually delivered to said patient with an amount of said therapeutic output expected to have been delivered to said patient based at least in part upon said predicted delivery rate and producing a result based thereon; and
   an adjusted parameter representative of an adjusted time in the future at which said therapeutic output delivery module should be replenished based at least in part upon said result from said comparator.

25. An implantable medical device as in claim 24 further comprising a communication module operatively coupled to said adjusted parameter and capable of communicating with an external device.

26. An implantable medical device as in claim 24 wherein said therapeutic output delivery module comprises a reservoir for holding a therapeutic substance and a pump operatively coupled to said reservoir for delivering said therapeutic substance to said patient.

27. An implantable medical device as in claim 26 wherein said measure comprises a count of an amount of delivery of said pump.

28. An implantable medical device as in claim 26 wherein said measure comprises a volume of said therapeutic substance.

29. An implantable medical device as in claim 24 wherein said therapeutic output is delivered to said patient at a variable rate.

30. An implantable medical device as in claim 29 wherein said variable rate is at least partially controlled by said patient.

31. An implantable medical device as in claim 30 wherein said variable rate is at least partially determined by a patient-controlled bolus.

32. An implantable medical device as in claim 24 wherein said calculator determines said parameter using simple arithmetic.

33. An implantable medical device as in claim 32 wherein said simple arithmetic comprises addition and subtraction.

34. An implantable drug pump as in claim 32 wherein said adjusted parameter is determined by subtracting an amount from said adjusted parameter based at least in part on said result.

35. An implantable drug pump as in claim 34 wherein said subtracting decrements said adjusted parameter.

36. An implantable medical device as in claim 24 wherein said determining is accomplished periodically.

37. An implantable medical device as in claim 36 wherein said determining is accomplished daily.

38. An implantable medical device as in claim wherein 24 said replenishment comprises refilling a reservoir with a therapeutic substance.

39. An implantable medical device as in claim 24 wherein said replenishment comprises replacing at least a portion of said therapeutic output delivery module.

40. An implantable medical device as in claim 24 wherein said replenishment comprises replenishing a power source in said therapeutic output delivery module.

41. An implantable drug pump for delivering a variable amount of a therapeutic substance to a patient into which said implantable drug pump is implanted, comprising:
   a reservoir for holding said therapeutic substance;
   a pump operatively coupled to said reservoir and adapted to be coupled to said patient to deliver said therapeutic substance to said patient;
   a predetermined parameter representative of a time in the future at which said reservoir of said implantable drug pump should be replenished based at least in part upon a predicted delivery rate of said therapeutic substance to said patient;
   a measure determining an amount based at least in part on a quantity of said therapeutic substance actually delivered to said patient;
   a comparator operatively coupled to said predetermined parameter and to said counter for comparing said amount with an amount of said therapeutic substance expected to have been delivered to said patient based at least in part upon said predicted delivery rate and producing a result based thereon; and
   an adjusted parameter representative of an adjusted time in the future at which said reservoir of said implantable drug pump should be replenished with said therapeutic substance based at least in part upon said result from said comparator.

42. An implantable drug pump as in claim 41 further comprising a communication module operatively coupled to said adjusted parameter and capable of communicating with an external device.

43. An implantable medical device as in claim 41 wherein said measure comprises a count of an amount of delivery of said pump.

44. An implantable medical device as in claim 41 wherein said measure comprises a volume of said therapeutic substance.

45. An implantable medical device as in claim 41 wherein said therapeutic substance is delivered to said patient at a variable rate.

46. An implantable medical device as in claim 45 wherein said variable rate is at least partially controlled by said patient.

47. An implantable medical device as in claim 46 wherein said variable rate is at least partially determined by a patient-controlled bolus.

48. An implantable medical device as in claim 41 wherein said calculator determines said parameter using simple arithmetic.

49. An implantable medical device as in claim 48 wherein said simple arithmetic comprises addition and subtraction.

50. An implantable drug pump as in claim 41 wherein said adjusted parameter is determined by subtracting an amount from said adjusted parameter based at least in part on said result.

51. An implantable drug pump as in claim 50 wherein said subtracting decrements said adjusted parameter.

52. An implantable medical device as in claim 41 wherein said determining is accomplished periodically.

53. An implantable medical device as in claim 52 wherein said determining is accomplished daily.

54. An implantable medical device as in claim wherein 41 said replenishment comprises refilling said reservoir with a therapeutic substance.

* * * * *